United States Patent [19]

Smith-Lewis

[11] Patent Number: 4,870,007

[45] Date of Patent: Sep. 26, 1989

[54] IMMOBILIZED BIOTINYLATED RECEPTOR IN TEST DEVICE, KIT AND METHOD FOR DETERMINING A LIGAND

[75] Inventor: Margaret J. Smith-Lewis, Pittsford, N.Y.

[73] Assignee: Eastman Kodak Company, Rochester, N.Y.

[21] Appl. No.: 136,211

[22] Filed: Dec. 18, 1987

[51] Int. Cl.⁴ .................. C12Q 1/28; G01N 33/566
[52] U.S. Cl. ............................... 435/28; 435/7; 436/501; 436/531; 436/532
[58] Field of Search .............. 436/531, 532, 501; 435/7, 28

[56] References Cited

U.S. PATENT DOCUMENTS

| | | | |
|---|---|---|---|
| 3,666,421 | 5/1972 | Price | 23/253 |
| 3,964,870 | 6/1976 | Tiedemann et al. | |
| 3,970,429 | 7/1976 | Updike | 23/230.6 |
| 3,975,162 | 8/1976 | Renn | 23/253 |
| 4,210,420 | 7/1980 | Baughman et al. | |
| 4,234,316 | 11/1980 | Hevey | 23/230 R |
| 4,298,685 | 11/1981 | Parikh et al. | 435/7 |
| 4,387,164 | 6/1983 | Hevey et al. | 436/45 |
| 4,444,879 | 4/1984 | Foster et al. | 436/532 |
| 4,486,530 | 12/1984 | David et al. | |
| 4,496,654 | 1/1985 | Katz et al. | 435/7 |
| 4,496,658 | 1/1985 | Kondo et al. | |
| 4,503,143 | 3/1985 | Gerber et al. | |
| 4,530,900 | 7/1985 | Marshall | 435/7 |
| 4,582,810 | 4/1986 | Rosenstein | 436/532 |
| 4,650,751 | 3/1987 | Siegel et al. | 435/7 |

FOREIGN PATENT DOCUMENTS

| | | |
|---|---|---|
| 0042755 | 12/1981 | European Pat. Off. |
| 0188093 | 7/1986 | European Pat. Off. |
| 0201079 | 11/1986 | European Pat. Off. |
| 210863 | 2/1987 | European Pat. Off. |
| 57-201853 | 12/1982 | Japan |
| WO87/03690 | 6/1987 | PCT Int'l Appl. |
| WO87/04794 | 8/1987 | PCT Int'l Appl. |
| 1523581 | 9/1978 | United Kingdom |

OTHER PUBLICATIONS

Toray-Derwent Abstract of Japanese J6-0024-450-A, 1985.
Odell et al, *Clin. Chem.*, 32 (10), pp. 1873–1878 (1986).
Publication No. GCG0229 (Oct. 1988) for Kodak Surecell ™ hCG-Urine Test Kit, pp. 1–16.

*Primary Examiner*—Sam Rosen
*Attorney, Agent, or Firm*—J. Lanny Tucker

[57] ABSTRACT

A device useful for the determination of a ligand in an aqueous liquid comprises a water-insoluble substrate. Immobilized in at least one location on that substrate is a biotinylated receptor for the ligand. This receptor is in dried form and immobilized with one or more dried water-soluble acrylamide homo- or copolymer binder materials. When the immobilized receptor is contacted with an aqueous sample, the binder material is dissolved and the receptor is released for reaction with the ligand. The resulting reaction product is determined in a suitable manner. The device can be included in a kit having other components useful for ligand determination. The device and method of its use are particularly useful for the determination of human chorionic gonadotropin (hCG) as an early indicator of pregnancy.

22 Claims, No Drawings

IMMOBILIZED BIOTINYLATED RECEPTOR IN TEST DEVICE, KIT AND METHOD FOR DETERMINING A LIGAND

FIELD OF THE INVENTION

The present invention relates to a device and a method for its use to determine a ligand in aqueous liquids, such as biological fluids. It also relates to a kit which includes the device.

BACKGROUND OF THE INVENTION

There is a continuous need in medical practice, research and diagnostic procedures for rapid, accurate, qualitative or quantitative determinations of biological substances which are present in biological fluids at low concentrations. For example, the presence of drugs, narcotics, hormones, steroids, polypeptides, prostaglandins or infectious organisms in blood, urine, saliva, vaginal secretions, seminal fluids and other biological fluids has to be determined in an accurate and rapid fashion for suitable diagnosis or treatment.

To provide such determinations, various methods have been devised for isolating and identifying biological substances employing specific binding reactions between the substance to be detected (identified as a "ligand" herein) and receptors specifically reactive with that substance. Radioactive or enzyme labels have been used to detect the resulting reactive complex.

One particular type of test which has been developed is what is known in the art as an immunometric or a "sandwich" assay. Such an assay involves "sandwiching" the ligand (such as an antigen) with two or more receptor molecules (such as antibodies) which complex with the compound in a noninterfering manner and at different epitopic sites. Examples of such assays are described in U.S. Pat. No. 4,486,530 (issued Dec. 4, 1984 to David et al) where monoclonal antibodies having high affinity are used. In most sandwich assays, one or more of the receptor molecules are suitably immobilized on an insoluble carrier such as small particles, membranes, plates, or similar objects, as described in U.S. Pat. No. 4,496,654 (issued Jan. 29, 1985 to Katz et al) where a biotinylated antibody is immobilized on an avidin coated support. U.K. Pat. No. 2,074,727 describes sandwich assays in which the complex of antigen and antibodies formed is or will be insolubilized at the time of or subsequent to complex formation.

Avidin is a protein found in egg whites. Biotin, or hexahydro-2-oxo-1H-thieno[3,4]imidazole-4-pentanoic acid (also known as Vitamin H), is a relatively small water-soluble molecule. These materials are known to react specifically with each other to form a very strong and stable complex in which each of the four subunits of avidin binds a biotin molecule. This trong binding is maintained even when either biotin or avidin or both are bound covalently to other materials.

E.P. Publication 201,079 (published Nov. 12, 1986) describes sandwich assays in which the complex of ligand and two receptors is formed in solution. One of the receptors (for example an antibody) is conjugated with either biotin or avidin. A support having biotin or avidin attached thereto is used to insolubilize the resulting ternary complex. While the assay of E.P. 201,079 allegedly provides certain advantages over assays using antibodies directly bound to the insoluble carrier, the assay is carried out by combining individual quantities of all reactants in a test chamber (such as a test tube).

It would be highly useful to have assays designed for mass production in which a minimal number of individually added liquid reagents and mixing steps are needed to determine the ligand. It would be desired to incorporate one or more reagents in a test device used to carry out the assay. U.S. Pat. No. 4,234,316 (issued Nov. 8, 1980 to Hevey) describes a device for delivering measured quantities of reagents into a solution assay medium. The reagents, including antibodies or antigens, are immobilized in the device using any of a wide variety of water-soluble binder materials.

However, there is a further need in the art beyond merely incorporating reagents in a test device for convenient reagent delivery. Those reagents must also be stable for long periods of time. For example, if a kit for an assay is to be transported long distances and stored indefinitely before use, it is necessary that any stored reagents be stable to various environmental conditions during that period of time. Many proteins which might be used as receptor molecules for determination of ligands in patient samples are not generally stable at room temperature for long periods of time. In particular, I have found that the use of biotinylated antibodies or antigens presents a special problem not addressed in the art. For a reason yet unknown, biotinylated antibodies have limited keeping stability.

SUMMARY OF THE INVENTION

The problems noted above have been overcome with the present invention which provides a device useful for the determination of a ligand in an aqueous liquid, the device comprising a water-insoluble substrate and having in one or more locations of the substrate, a biotinylated receptor for the ligand which is immobilized in dry form with one or more dried water-soluble acrylamide homo- or copolymers having at least 50 weight percent of acrylamide.

Also provided is a test kit for the determination of a ligand in an aqueous liquid, the test kit comprising:
  the device described above, and
  a detection system for detecting the formation of a reaction complex between the ligand and the biotinylated receptor.

A method for the determination of a ligand in an aqueous liquid comprises the steps of:
  A. contacting a sample of the liquid with the device described above to form a reaction product of the ligand with the receptor, and
  B. determining the presence or absence of the reaction product.

The device, kit and method of the present invention provides a rapid and accurate means for detecting qualitatively or quantitatively the presence or absence of a ligand in a fluid sample. The kit has a number of necessary and optional components, but the number of solutions and mixing steps are minimized.

More importantly, the device contains one or more biotinylated receptors which are stable over an extended period of time. These advantages are achieved by immobilizing the receptors in the device in dry form with one or more dried water-soluble acrylamide homo- or copolymers. Such binder materials effectively improve keeping of the receptor during manufacture, transport and storage and are readily solubilized by the aqeuous fluid sample during the assay, thereby making the biotinylated receptor available for reaction with the ligand of interest in the fluid sample. As indicated below in Examples 2 and 3, however, not every water-soluble binder material will provide the desired keeping stability. Only the acrylamide polymers defined herein provide the unexpected keeping stability achieved with the present invention.

DETAILED DESCRIPTION OF THE INVENTION

The present invention provides a device and method for use in analytical methods whereby a detectable complex between ligand and receptor is obtained. The method can be used to provide a determination so that an assay can be performed in a doctor's office or in a onsumer's home to provide immediate results. The assay can be used to detect the presence or absence of a mono- or multivalent or multideterminant compound of biological interest in an aqueous liquid, such as a biological fluid. Preferably, it is used to detect a multideterminant compound, such as hCG.

More specifically, the present invention can be used in the determination (qualitative or quantitative measurement) of a ligand in aqueous liquids to which there are naturally occurring or synthetically produced specific binding receptors. This determination can be made by merely determining the presence or absence of the ligand, or by quantitatively determining the amount of ligand. In particular, the invention can be used to assay biological fluids of animals, humans or plants, but preferably of humans. Such fluids include, but are not limited to, whole blood, plasma, sera, lymph, bile, urine, spinal fluid, seminal fluid, lacrimal fluid, vaginal secretions, sputum, perspiration and the like as well as stool specimens. It is also possible to assay fluid preparations of human or animal tissue such as skeletal muscle, heart, kidney, lungs, brains, bone marrow, skin and the like.

A monovalent ligand has a single epitopic site for complexation. A multivalent ligand has two or more epitopic sites for complexing with a multiplicity of the same specific binding receptor. A multideterminant ligand has two or more epitopic sites for complexing with a multiplicity of different receptors.

The ligand of interest can be an immunological species which is (1) any substance which, when presented to an immunocompetent host, will result in the production of a specific antibody capable of binding with that substance, or (2) the antibody so produced, which ligand participates in an antigen-antibody reaction.

In the present invention, biotin or a biotin derivative is suitably attached to the receptor molecule which reacts specifically with the ligand. Attachment procedures are well known in the art. A specific procedure is described below in Example 1.

Representative ligands detectable with the present invention include primary amines, amino acids, peptides, polypeptides, proteins, lipoproteins, glycoproteins, drugs, haptens, enzymes, steroids, lipids, nucleic acids, hormones, vitamins, polysaccharides, glycolipids, alkaloids, organisms (bacteria, protozoa, fungi, viruses including retroviruses, rickettsia and the like) and components thereof, blood components, tissue and organ antigens and other materials known to one skilled in the art. In some instances, the ligand is an antibody which is directed against a drug, hormone, antibiotic or other compound having antigenic properties. Where the ligand is an antigen and the receptor is an antibody, either monoclonal and polyclonal antibodies can be used, and they can be whole molecules or various fragments thereof. Preferably, biotinylated monoclonal antibodies are used in the present invention.

In a preferred embodiment, the invention is useful for the detection of hCG as an early indicator of pregnancy. In this embodiment, one or more different antibodies to hCG are immobilized in the test device, as described below, in order to provide reagents for forming an immunological complex with hCG at different epitopic sites. At least one of these antibodies is biotinylated.

As noted above, the kit of the present invention includes the device described herein, as well as a detection system for detecting the formation of a reaction complex between the ligand and its biotinylated receptor.

In general, the device of this invention comprises a water-insoluble substrate which is chemically and immunologically inert (that is, nonreactive) with the ligand, receptor or other reagents used in the assay. The substrate can be a flat test slide, paper, cup, petri dish, test tube, plate, membrane or other suitable configured material which will accommodate one or more reagents and which can be contacted in some manner with a test fluid. Either the fluid can be added to the device, such as a test tube or microtest plate, or the device can be added to the test fluid or otherwise contacted for a period of time sufficient for the assay to occur. The device can be disposable or reuseable.

In one embodiment, the device canbe used to react ligand and receptor, but the resulting complex is then put into a second device in which the amount of ligand is determined in a suitable fashion. Alternatively, the device can be a device where the assay is carried out, such as a microtest plate having a multiplicity of preformed test wells. Various test devices are known in the art including U.S. Pat. Nos. 3,825,410 (issued July 23, 1974 to Bagshawe), 3,888,629 (issued June 10, 1975 to Bagshawe), 3,970,429 (issued July 20, 1976 to Updike) and 4,446,232 (issued May 1, 1984 to Liotta). One useful device is illustrated in copending and commonly assigned U.S.S.N. 98,248, filed Sept. 18, 1987 by Hinckley et al and entitled "Sliding Valve for Vent of Liquid Collecting Compartment", and in copending and commonly assigned U.S.S.N. 136,164, filed on even date herewith by myself and entitled "Test Device With Dried Reagent Drops on Inclined Wall", the disclosures of both of which are incorporated herein by reference.

The device of this invention can be a device whereby the reagents are mixed for later use in an assay in a different device or container. Preferably, the device is designed as a test device for both reagent mixing and testing either in the same or a different location of the device.

More specifically, the test device of this invention comprises a water-insoluble substrate having one or more test zones therein each of which can accommodate a sample of a biological fluid and appropriate reagents.

The substrate can be prepared from any useful water-insoluble material such as glass, polymeric materials, fibrous materials, cellulosic materials and other materials known in the art to which the biotinylated antibody can be immobilized using the polymeric binder materials described below.

In a preferred embodiment, the test device has three test zones or wells designed for providing a test result and positive and negative control results. Such a device would be particularly useful in a doctor's office or in a consumer's home as part of a diagnostic kit, such as a pregnancy test kit. For example, the device described in U.S.S.N. 98,248 (noted above) comprises at least one liquid-collecting well (or, as described herein, a test well), means in that compartment defining a vent aperture fluidly connecting the compartment to the atmosphere, and a closure means for shutting off the vent aperture. Preferably, the test device has three separate test wells, one for a test sample, a second for a negative control and a third for a positive control. Another test device is described and claimed in copending and commonly assigned U.S.S.N. 19,810, filed Feb. 27, 1987 by Hinckley. Other variations of useful test devices would be within the purview of a worker of ordinary skill in the art.

The device of this invention is adaptable to any assay using suitable chemical and biological reagents. It is essential, however, that it has at least one biotinylated receptor for the ligand immobilized therein. If desired, one or more test zones of the device can have the same or a different receptor immobilized therein. In some instances, a single test zone can have more than one receptor immobilized therein as long as those receptors are such that they do not interfere with each other, or are immobilized in such a manner that they do not interfere with each other.

The biotinylated receptor is immobilized on the substrate with the polymer described below in such a manner so that it is secured to the substrate in some manner. Generally the receptor and the polymer is admixed and secured to the substrate. Alternatively, the receptor can be secured to the substrate alone with the polymer coated over it. The polymer and receptor can be applied in several alternating layers if desired. In any of these embodiments, humectants, surfactants or desiccants can be optionally included with the biotinylated receptor, polymer or both. Generally, biotinylated receptor and polymeric binder material are incorporated together and immobilized in the device in an aqueous solution, then dried under suitable conditions.

Useful water-soluble polymeric binder materials include polymeric materials which readily dissolve in aqueous media and which are inert to complex formation between ligand and receptor as well as to any other chemical or specific binding reactions which may occur in an assay. More specifically, useful polymeric binder materials are acrylamide homo- and copolymers. Useful copolymers are prepared from two or more ethylenically unsaturated polymerizable monomers, at least 50 weight percent of the combined monomer weight being acrylamide. Useful polymeric binder materials include, but are not limited to, poly(acrylamide), poly(acrylamide-co-1-vinyl-2-pyrrolidone)(90:10 weight ratio), poly-(acrylamide-co-1-vinyl-2-pyrrolidone)(50:50 weight ratio), poly(acrylamide-co-1-vinylimidazole)(90:10 weight ratio), poly(acrylamide-co-2-methyl-1-vinylimidazole)(90:10 weight ratio), poly(acrylmide-co-N-methylolacrylamide)(80:20 weight ratio), poly(acrylamide-co-acrylic acid)(90:10 weight ratio), poly(acrylamide-co-2-vinylpyridine)(89:11 weight ratio), poly(acrylamide-co-2-methyl-5-vinylpyridine)(90:10 weight ratio) and poly(acrylamide-co-1-vinyl-2-pyrrolidone-co-acrylic acid)(75:15:10 weight ratio). Poly(acrylamide) is a preferred material. More than one binder material can be used if desired, and different binder materials can be used for different receptors or in different zones of the device.

The ratio of binder material to receptor can be varied widely depending upon the assay being conducted and the amount of receptor needed for a given ligand. Generally, the amount of receptor immobilized is at least 0.01 $\mu$g, with from about 1 to about 10 $\mu$g being preferred, but this will depend upon the ligand to be determined. Generally, the ratio of binder material to receptor is from about 1:1 to about 100:1. The biotinylated receptor and binder material are generally mixed in a suitable fashion and deposited in the device and dried prior to use in a suitable manner. In most instances, the drying process takes less than two hours. For example, the binder material and receptor are mixed in a buffer in a glass test tube and applied to the side of a test well of a test device (such as that described in U.S.S.N. 98,248, described above) and air dried.

As defined above, the immobilized biotinylated receptor is a compound which specifically complexes with the ligand. Most often, this receptor is an antibody to a ligand which has antigenic properties. However, it can also be an antigen if the ligand is an antibody, or the receptor can be an antibody to an antibody. The immobilized receptor is biotinylated, such as a biotinylated antigen or antibody prepared using known procedures and reagents [see for example, E.P. Publication 201,079, noted above, and U.S. Pat. Nos. 4,276,206 (issued June 30, 1981 to Katz) and 4,298,685 (issued Nov. 3, 1981 to Parikh et al)].

The device of this invention can also have other reagents incorporated therein in a suitable manner. For example, a buffer can be immobilized therein, such as by drying a buffer in a region of the test device. These reagents can also be immobilized with the same or different binder material as that used for the biotinylated receptor. It is important that any other incorporated materials be functionally isolated from other reagents (such as the biotinylated receptor) prior to the assay. This can be done by immobilizing those additional materials in a location different from that of the immobilized receptor, or by using protective materials, coatings and the like (for example, encapsulation or protective coatings). It can also be accomplished by immobilizing reagents together that require an activating agent of some type for reaction.

As noted above, the kit of this invention also includes a detection system for detecting the formation of a ligand-receptor complex. This composition can be as simple as a second receptor for the ligand, which second receptor is suitably labeled for detection. Useful detection moieties include, but are not limited to, radioisotopes, chemiluminescent compounds, bioluminescent compounds, fluorescent compounds, colored beads, dyes, dye precursors and enzymes. Many useful labels are described in the art, for example, in E.P. Publication 201,079 (noted above). These labels can be detected using suitable reagents, equipment and procedures.

Preferably, the label is an enzyme (for example, peroxidase, alkaline phosphatase, malate dehydrogenase, glucose oxidase, urease, catalase or glucose-6-phosphate dehydrogenase). In such as case, the kit optionally includes an enzyme substrate and a dye-providing composition if needed. Reaction of the enzyme on the substrate may provide a detectable species. Alternatively, other dye-forming materials and reactions may be needed for providing a detectable species, such as a dye.

For example, when peroxidase is used as a label, the kit could also include hydrogen peroxide and appropriate dye-forming reagents, such as a tetramethylbenzidine or a leuco dye which provides a dye in the presence of hydrogen peroxide and peroxidase [for example, a triarylimidazole leuco dye as described in U.S. Pat. Nos. 4,089,747 (issued May 16, 1978 to Bruschi) or a triarylmethane leuco dye as described in 4,670,385 (issued June 2, 1987 to Babb et al)]. A preferred dye-providing composition is described and claimed in copending and commonly assigned U.S.S.N. 136,166, filed on even date herewith by McClune et al and entitled "Dye-Providing Composition, Diagnostic Test Kit and Their Use in Method for Ligand Determination Using Peroxidase Labeled-Receptor". Useful substrates and dye-forming reagents for other useful enzymes are well within the skill of an ordinary worker in the art.

In a preferred embodiment of this invention, the test kit comprises:

(a) an insolubilizing reagent comprising an insoluble phase to which avidin is bound, (b) a test device comprising a water-insoluble substrate having one or more test zones, and having in at least one of the test zones, a biotinylated receptor for the ligand which is in dry form and immobilized with one or more dried water-soluble acrylamide homo- or copolymers having at least 50 weight percent of acrylamide, the biotinylated receptor being capable of reacting with the ligand at a first epitopic site as well as with avidin, and (c) a second receptor for the ligand which is labeled and is capable of reacting with the ligand at a second epitopic site but which is incapable of reaction with avidin.

The insolubilizing reagent of this preferred kit has an insoluble phase, such as glass beads, metal particles, membranes, polymeric beads, glass or cellulosic fibers, and others known in the art, to which are attached molecules of avidin or a derivative thereof, such as streptavidin, succinylated avidin, monomeric avidin and the like.

Avidin or a derivative thereof can be attached to an insoluble phase in any suitable fashion known in the art, for example, as described in U.S. Pat. Nos. 4,298,685 (noted above), 4,496,654 (noted above) and 4,582,810 (issued Apr. 15, 1986 to Rosenstein) and PCT Publication 84/03358 (published Aug. 30, 1984). The avidin can be attached by adsorption, but preferably it is attached covalently by reaction of reactive moieties in the avidin molecule (such as reactive amine groups) with the appropriate reactive groups on the carrier (such as carboxyl, halomethyl, vinylsulfonyl or chloroethylsulfonyl).

A preferred insolubilizing reagent useful in the practice of this invention is described in copending and commonly assigned U.S.S.N. 136,165, filed on even date herewith by Sutton et al and entitled "Avidin- and Biotin-Immobilized Reagents, Analytical Elements and Methods of Use". A representative reagent is described and used in Example 1 below. These preferred reagents are prepared by covalently attaching avidin to the insoluble phase, for example, polymeric beads, through activated 2-substituted ethylsulfonyl or vinylsulfonyl groups or active halogen atoms.

The preferred kit described above includes a test device having one or more test zones and having an immobilized biotinylated receptor which is capable of reacting with the insolubilizing reagent. Preferably, this receptor is a biotinylated antigen or antibody. Most preferably, it is a biotinylated antibody.

The second receptor mentioned above in the kit reacts with the ligand at an epitopic site different from the epitopic site of reaction between the ligand and the biotinylated receptor. This second receptor is generally labeled with a suitable label, for example, as described above. It also can be immobilized in the test device using a suitable binder material, which material can be the same or different than that used to immobilize the biotinylated receptor.

For example, a kit useful for the determination of hCG has the following components:

(a) an insolubilizing reagent comprising an insoluble phase to which avidin is bound, (b) a test device comprising a water-insoluble polymeric substrate having a multiplicity of test wells, and having immobilized in at least one of the test wells, a biotinylated antibody reactive with hCG at a first epitopic site, which antibody is in dry form and admixed with one or more dried, water-soluble acrylamide homo- or copolymers having at least 50 weight percent of acrylamide, and (c) a second antibody for hCG which is labeled and which is capable of reacting with hCG at a second epitopic site.

The kit of the present invention can also include optional reagents and equipment such as wash solutions, buffer solutions, reagent solutions, bottles, pipettes, devices for prefiltering specimens and other materials known in the art which facilitate kit use.

Generally, the method of this invention is carried out by contacting the device with a sample of liquid suspected of containing the ligand in such a manner as to form a reaction product of any ligand present and the biotinylated receptor in the test device. The liquid sample dissolves the binder material, making the receptor available for reaction. Preferably, the liquid sample is applied to a test zone of the device or placed in a test well, depending upon the configuration of the device. The presence or absence of the reaction product is then determined in a suitable manner, for example using light scattering, colorimetric, fluorometric, radiometric or other techniques.

The method of the invention can be a competitive binding immunoassay using both labeled and unlabeled receptor. Either bound (that is, complexed) or unbound (that is, uncomplexed) materials can be determined. Physical separation of bound and unbound materials, if desired, can be carried out using any suitable separation technique.

In a preferred embodiment, the method is what is known in the art as an immunometric assay. The details of such assays are provided in U.S. Pat. No. 4,486,530 (noted above). Such an assay can be used to to determine multivalent or multideterminant ligands as described above, that is ligands having two or more epitoic sites for immunological reaction with two or more receptor molecules. In the sandwich assay, a second receptor is brought into contact with the ligand either prior to, simultaneously with or subsequent to contact of the ligand with the test device (and hence, contact of the ligand with the first receptor). The result is the formation of a immunological complex of the two distinct receptors with the ligand. At least one of the receptors is biotinylated. Most preferably, the first receptor is biotinylated. The resulting complex is insolubilized when the avidin on an insoluble phase and biotin as part of the first receptor react, and the resulting insolubilized complex can be separated from unreacted material in the test device. One of the receptors or the insoluble phase can be labeled suitably for detection of the insolubilized complex.

In a preferred embodiment, a method for the determination of hCG in an aqueous liquid comprises the steps of:

A. contacting a sample of the liquid with a test device comprising a water-insoluble substrate having one or more test zones, and having immobilized in at least one of the test zones, a biotinylated antibody to hCG which is in dry form and admixed with one or more dried water-soluble acrylamide homo- or copolymers having at least 50 weight percent of acrylamide, to form a reaction product of hCG with the biotinylated antibody at a first epitopic site, B. prior to, simultaneously with or subsequent to the contacting step (A), contacting the liquid sample with a second antibody to hCG which is labeled and which reacts with hCG at a second epitopic site, to form a complex of hCG with the first and second antibodies, C. contacting the ternary complex with an insolubilizing reagent comprising an insoluble phase to which avidin is bound, to form an insolubilized complex through reaction of avidin with biotin, D. separating the resulting labeled, insolubilized complex from unreacted materials, and E. determining the presence or absence of the labeled insolubilized complex.

This method can be practiced in a doctor's office or at home for early determination of pregnancy by assayng urine samples.

The following examples are representative of the practice of this invention but are not intended to limit the scope of this invention.

MATERIALS

Antibody-biotin conjugates were prepared using anti-hCG monoclonal antibodies obtained from Immuno-Search, Inc. (Toms River, N.J.) and biotin N-hydroxysuccinimide obtained from Calbiochem-Behring Corp. using the method described by Hofmann et al, J.A.C.S. 100, 3585 (1978).

Human chorionic gonadotropin (hCG) was obtained from Calbiochem (La Jolla, Calif.).

Antibody-peroxidase conjugates were prepared using anti-hCG monoclonal antibodies obtained from Cambridge Medical Diagnostics (Bellerica, Mass.) and horseradish peroxidase from Miles Laboratories (Elkhart, Ind.) by the method described by Yoshitake et al, *Eur. J. Biochem.* 101, 395 (1979).

A leuco dye solution was prepared with 2-(4-hydroxy-3,5-dimethoxyphenyl)-4,5-bis(4-methoxyphenyl)imidazole as follows:

Solid leuco dye (to make a 0.1% solution) was dissolved in a solution of 20% poly(vinyl pyrrolidone) in sodium phosphate buffer (5 mmolar). This solution was then added to a solution containing hydrogen peroxide (10 mmolar), 4'-hydroxyacetanilide electron transfer agent (5 mmolar) and diethylenetriaminepentaacetic acid chelating agent (10 $\mu$molar) in sodium phosphate buffer to produce a final concentration of 1% poly(vinyl pyrrolidone) and 0.005% leuco dye.

Succinylated casein was prepared by reacting casein with an equal weight of succinic anhydride for four hours at 25° C., then purifying the product by dialysis.

MOPS buffer is 3-(N-morpholino)propanesulfonic acid (pH 7.5) which is commercially available from a number of sources.

EXAMPLE 1

Assay of Urine for hCG

Preparation of Insolubilizing Reagent:

The following procedure for attachment of avidin to an insoluble phase is taken from Example 1 of copending U.S. Ser. No. 136,165 of Sutton et al, mentioned above.

The three solutions outlined below were continuously added to a 1365 ml vessel containing deoxygenated water at 80° C. at the indicated rates:

Solution 1: Styrene (739 g), m & p-(2-chloroethylsulfonylmethyl)styrene (82 g) and 1-dodecanethiol (8.2 g) at 2.5 g/min. for 380 minutes.

Solution 2: Ammonium persulfate (19.7 g) and distilled, deoxygenated water (1152 g) at 2.14 g/min. for 380 minutes.

Solution 3: Sodium pyrosulfite (9.9 g) and distilled water (1152 g) at 2.27 g/min. for 380 minutes.

After 380 minutes, the reaction was stopped, yielding about 1218 g of latex at 33.4% solids. The latex was dialyzed for 3 days to yield a latex having 27.3% solids and a pH of 5. This latex was diluted to 13.5% solids. NMR analysis confirmed at 96:4 molar ratio of styrene to the second monomer. The resulting latex particles had an average diameter of about 0.67 $\mu$m as measured by transmission electron microscopy.

A sample (0.75 ml) of the latex described above was diluted to 20 ml with borate buffer (50 mmolar, pH 8.5) and avidin (5 mg, Sigma Chemical Co.) was subsequently added. The resulting suspension was agitated in an end-over-end fashion at 37° C. for 18 hours, followed by centrifugation. The supernatant was discarded and the particles washed once with buffer by centrifugation and resuspended in 10 ml borate buffer. Biotin binding analysis (that is, titration with tritium labeled biotin) indicated that avidin had been covalently attached to the particles ($7 \times 10^{-6}$ molar binding sites per 0.3% bead suspension) to form a reagent of the present invention.

Assay

Test devices, as described in U.S. Ser. No. 98,248 (noted above), were used to determine hCG in a urine specimen in the following manner. Each test device comprised: a negative control well to show background and to act as a reference test, a positive control well to indicate that the reagents and procedures were used properly, and a test well for the assay. Each test well contained a filter membrane consisting of a microporous nylon filter membrane (obtained from Pall Corp.) which had been coated with succinylated casein (1.07 g/m$^2$).

Test device A was prepared according to this invention. The negative control test well contained MOPS buffer (2 mg) and poly(acrylamide) binder (60 $\mu$g). The test well for the assay contained a dried coating of biotinylated anti-hCG antibodies (3 $\mu$g) immobilized in poly(acrylamide) binder (60 $\mu$g), and dried MOPS buffer (2 mg) in a different location in the test well. The positive control well contained biotinylated anti-hCG antibodies (3 $\mu$g) immobilized in poly(acrylamide) binder (60 $\mu$g), and dried hCG (400 mI.U.) in a separate location from the MOPS buffer (2 mg) in the test well.

Test device B was prepared and tested as a Control device and contained the same materials as Test device A except that the antibodies were not immobilized in poly(acrylamide) binder.

Both test devices were kept at 25° C. and 50% relative humidity for 3 months.

Following the keeping time, the test devices were used to assay urine samples for hCG. These samples had been prefiltered to remove impurities and were known to contain about 50 mI.U./ml of hCG. The samples were added to all wells of each test device, followed by the addition of a peroxidase-labeled monoclonal anti-hCG antibody (40 μl of a $10^{-9}$ molar solution) to each well. After two minutes incubation period, a suspension of the insoluble immunoreactive reagent described above (40 μl of a 0.42% dispersion) was added and fluid was allowed to drain through the membrane in each well.

A wash solution (200 μl) comprising sodium phosphate (0.1 molar) and sodium dodecylsulfate (10 mmolar) was added to each well, followed by the addition of the leuco dye solution described above (40 μl). After two minutes, the color formed on each membrane was evaluated by reflectance measurements using standard equipment and the results were converted to transmittance density ($D_T$) using the Williams-Clapper transform.

The resulting data are shown in the following Table I as the difference ($\Delta D_T$) between the test sample well density and the negative control well density for each test device. The standard deviation is shown in parentheses. The data indicate that Test device A provided significant improvement in retained sensitivity for hCG determination because of the presence of poly(acrylamide) therein for immobilizing the biotinylated antibody.

TABLE I

|  | $D_T$ After Keeping Test |
|---|---|
| Test Device A (Invention) | 0.042 (0.006) |
| Test Device B (Control) | 0.000 (0.001) |

EXAMPLES 2-3

Comparison of Various Binder Materials

The assay described in Example 1 was repeated with several test devices in which the antibodies were immobilized therein using various binder materials. After incorporation of biotinylated antibody with the binder material, the test devices were kept at 25° C. and 50% relative humidity for 5 months.

The data are provided below in Table II as $D_T$ calculated both before the keeping test ("fresh") and after keeping test. The $D_T$ for the test and negative wells of each device were measured. A difference in $D_T$ of at least 0.008 units between the test well and negative test well both fresh and after keeping is considered necessary in order to obtain a positive determination of the antigen. If the difference is less than 0.008 units, the background is either too high, or the test device lacks sensitivity.

The results indicate that the polymeric binder materials used in Examples 1 [60 μg of poly(acrylamide)], 2 [30 μg of poly(acrylamide)] and 3 [60 μg of poly(acrylamide-co-1-vinyl-2-pyrrolidone)] are useful, with that of Example 1 being most preferred. The assay of Control A using 60 μg of poly(1-vinyl-2-pyrrolidone) was unacceptable even fresh and the assay of Control B using 60 μg of bovine serum albumin had too high a background and lacked sensitivity after 5 months keeping.

TABLE II

| Test Device | | $D_T$ Fresh | $D_T$ After Keeping Test |
|---|---|---|---|
| Example 1 | Test well | 0.041 | 0.020 |
|  | negative control well | 0.006 | 0.006 |
| Example 2 | test well | 0.042 | 0.017 |
|  | negative control well | 0.008 | 0.007 |
| Example 3 | test well | 0.021 | 0.014 |
|  | negative control well | 0.007 | 0.006 |
| Control A | test well | 0.012 | not tested |
|  | negative control well | 0.007 | not tested |
| Control B | test well | 0.035 | 0.016 |
|  | negative control well | 0.017 | 0.013 |

The invention has been described in detail with particular reference to preferred embodiments thereof, but it will be understood that variations and modifications can be effected within the spirit and scope of the invention.

I claim:

1. A device useful for the determination of a ligand in an aqueous liquid, said device comprising a water-insoluble substrate and having in one or more locations of said substrate, a biotinylated receptor for said ligand which is immobilized in dry form in admixture or overcoated with one or more dried water-soluble acrylamide homo- or copolymers having at least 50 weight percent of acrylamide.

2. The device of claim 1 wherein said biotinylated receptor comprises a biotinylated antibody to said ligand.

3. The device of claim 2 wherein said receptor is a biotinylated antibody to hCG.

4. The device of claim 1 wherein said biotinylated receptor is a biotinylated antigen.

5. The device of claim 1 comprising one or more test zones in which said biotinylated receptor is immobilized.

6. The device of claim 1 wherein said biotinylated receptor is immobilized with water-soluble poly(acrylamide).

7. A test device for the determination of hCG in an aqueous liquid, said device comprising a water-insoluble polymeric substrate having a multiplicity of test wells, and having immobilized in at least one of said test wells, a biotinylated antibody to hCG which is in dry form and admixed with a water-soluble acrylamide homopolymer or copolymer having at least 50 weight percent of acrylamide.

8. A test kit for the determination of a ligand in an aqueous liquid, said test kit comprising:
a device comprising a water-insoluble substrate and having in one or more locations of said substrate, a biotinylated receptor for said ligand which is immobilized in dry form in admixture or overcoated with one or moredried water-soluble acrylamide homo- or copolymers having at least 50 weight percent of acrylamide, and
a detection system for detecting the formation of a reaction complex between said ligand and said biotinylated receptor.

9. A test kit for the determination of a polyvalent ligand in an aqueous liquid, said test kit comprising:

(a) an insolubilizing reagent comprising an insoluble phase to which avidin or a derivative thereof is bound, (b) a test device comprising a water-insoluble substrate having one or more test zones, and having in at least one of said test zones, a biotinylated receptor for said ligand which is in dry form and immobilized in admixture or overcoated with one or more dried water-soluble acrylamide homo- or copolymers having at least 50 weight percent of acrylamide, said biotinylated receptor being capable of reacting with said ligand at a first epitopic site as well as with avidin, and (c) a second receptor for said ligand which is labeled and is capable of reacting with said ligand at a second epitopic site but which is incapable of reacting with avidin or its derivative.

10. The test kit of claim 9 wherein said biotinylated receptor is immobilized with water-soluble poly(acrylamide).

11. The kit of claim 9 wherein said second receptor is enzyme-labeled.

12. The kit of claim 11 wherein said second receptor is labeled with peroxidase.

13. The kit of claim 11 further comprising a substrate for said enzyme and a dye-providing composition which provides a dye upon interaction of said enzyme with said substrate.

14. A test kit for the determination of hCG in an aqueous liquid, said test kit comprising:

(a) an insolubilizing reagent comprising an insoluble phase to which avidin or a derivative thereof is bound, (b) a test device comprising a water-insoluble polymeric substrate having a multiplicity of test wells, and having immobilized in at least one of said test wells, a biotinylated antibody reactive with hCG at a first epitopic site, which antibody is in dry form and admixed with one or more dried water-soluble acrylamide homo- or copolymers having at least 50 weight percent of acrylamide, and (c) a second antibody for hCG which is labeled and which is capable of reacting with said ligand at a second epitopic site and is incapable of reacting with avidin.

15. The kit of claim 14 wherein each of said antibodies is monoclonal.

16. The kit of claim 14 wherein said second antibody is labeled with an enzyme, and said kit further comprises a substrate for said enzyme and a dye-providing composition which provides a dye upon interaction of said enzyme with said substrate.

17. The kit of claim 16 wherein said enzyme is peroxidase and said subtrate is hydrogen peroxide and said dye-providing composition is a leuco dye which provides a dye in the presence of hydrogen peroxide and peroxidase.

18. A method for the determination of a ligand in an aqueous liquid, the method comprising the steps of:

A. contacting a sample of said liquid with a device comprising a water-insoluble substrate and having in one or more locations of said substrate, a biotinylated receptor for said ligand which is immobilized in dry form in admixture or overcoated with one or more dried water-soluble acrylamide homo- or copolymers having at least 50 weight percent of acrylamide, to form a reaction product of said ligand with said receptor, and B. determining the presence or absence of said reaction product.

19. The method of claim 18 for the determination of a polyvalent ligand comprising further contacting said liquid sample, prior to, simultaneously with or subsequent to said contacting step (A), with a second receptor which is capable of reacting with said ligand at an epitopic site different from the epitopic site of reaction of said immobilized receptor with said ligand.

20. A method for the determination of hCG in an aqueous liquid, the method comprising the steps of:

A. contacting a sample of said liquid with a test device comprising a water-insoluble substrate having one or more test zones, and having immobilized in at least one of said test zones, a biotinylated antibody to hCG which is in dry form and admixed with one or more dried water-soluble acrylamide homo- or copolymers having at least 50 weight percent of acrylamide, to form a reaction product of hCG with said biotinylated antibody at a first epitopic site, B. prior to, simultaneously with or subsequent to said contacting step (A), contacting said liquid sample with a second antibody to hCG which is labeled and which reacts with hCG at a second epitopic site, to form a complex of hCG with said first and second antibodies, C. contacting said complex with an insolubilizing reagent comprising a insoluble phase to which avidin is bound, to form an insolubilized complex through reaction of avidin with biotin, D. separating the resulting labeled, insolubilized complex from unreacted materials, and E. determining the presence or absence of said labeled, insolubilized complex.

21. The method of claim 20 wherein said second antibody is labeled with an enzyme, and said method further comprises adding a substrate for said enzyme and a dye-providing composition to said test device during or after the formation of said ternary complex.

22. The method of claim 20 for the determination of hCG in a urine sample.

* * * * *